United States Patent
Ku

(10) Patent No.: US 6,239,138 B1
(45) Date of Patent: May 29, 2001

(54) VITRONECTIN RECEPTOR ANTAGONIST

(75) Inventor: Thomas W. Ku, Dresher, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/445,636

(22) PCT Filed: Jul. 23, 1998

(86) PCT No.: PCT/US98/15271

§ 371 Date: Dec. 8, 1999

§ 102(e) Date: Dec. 8, 1999

(87) PCT Pub. No.: WO99/05107

PCT Pub. Date: Feb. 4, 1999

Related U.S. Application Data

(60) Provisional application No. 60/053,789, filed on Jul. 25, 1997.

(51) Int. Cl.$^7$ ................... A61K 31/435; A61K 31/44; C07D 213/00
(52) U.S. Cl. .................. 514/277; 546/1; 546/312; 514/352
(58) Field of Search .................. 514/277, 352; 546/1, 312

(56) References Cited

U.S. PATENT DOCUMENTS

| | | | |
|---|---|---|---|
| 5,373,023 | 12/1994 | Williams et al. | 514/165 |
| 5,723,450 | 3/1998 | Reuschling et al. | 514/63 |
| 5,770,613 | 6/1998 | Gaeta et al. | 514/332 |

FOREIGN PATENT DOCUMENTS

9915506 * 4/1999 (WO) .

* cited by examiner

*Primary Examiner*—Mukund J. Shah
*Assistant Examiner*—Sudhaker B. Patel
(74) *Attorney, Agent, or Firm*—Mary E. McCarthy; Stephen Venetianer; Charles M. Kinzig

(57) ABSTRACT

Compounds of the formula (I):

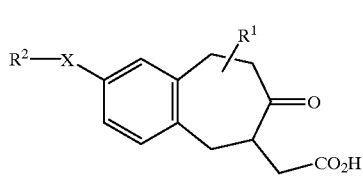

are vitronectin receptor antagonists useful in the treatment of osteoporosis.

14 Claims, No Drawings

VITRONECTIN RECEPTOR ANTAGONIST

This application claims benefit to Provisional Application 60/053,789 filed Jul. 25, 1997.

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases herein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpIIb/IIIa, the fibrinogen receptor, and $\alpha_v\beta_3$, the vitronectin receptor. The fibrinogen receptor gpIIb/IIIa is expressed on the platelet surface and it mediates platelet aggregation and the formation of a hemostatic clot at the site of a bleeding wound. Philips, et al., *Blood.,* 1988, 71, 831. The vitronectin receptor ($\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the bone resorption process and contributes to the development of osteoporosis. Ross, et al., *J. Biol. Chem.,* 1987, 262, 7703. The $\alpha_v\beta_3$ receptor expressed on human aortic smooth muscle cells stimulates their migration into neointima, which leads to the formation of atherosclerosis and restenosis after angioplasty. Brown, et al., Cardiovascular Res., 1994, 28, 1815. Additionally, a recent study has shown that a $\alpha_v\beta_3$ antagonist is able to promote tumor regression by inducing apoptosis of angiogenic blood vessels. Brooks, et al., *Cell,* 1994, 79, 1157. Thus, agents that would block the vitronectin receptor would be useful in treating diseases mediated by this receptor, such as osteoporosis, atherosclerosis, restenosis and cancer.

The vitronectin receptor is known to bind to bone matrix proteins, such as osteopontin, bone sialoprotein and thrombospondin, which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 disclose that echistatin, a snake venom peptide which contains the RGD sequence, is a potent inhibitor of bone resorption in tissue culture, and inhibits attachment of osteoclasts to bone. Fisher, et al., *Endocrinology* 1993, 132, 1411, has further shown that echistatin inhibits bone resorption in vivo in the rat. Bertolini et al., *J. Bone Min. Res.,* 6, Sup. 1, S146, 252 have shown that cylco-S,S-$N^\alpha$-acetyl-cysteinyl-$N^\alpha$-methyl-argininyl-glycyl-aspartyl-penicillamine inhibits osteoclast attachment to bone. EP 528 587 and 528 586 report substituted phenyl derivatives which inhibit osteoclast mediated bone resorption.

Alig et al., EP 0 381 033, Hartman, et al., EP 0 540,334, Blackburn, et al., WO 93/08174, Bondinell, et al., WO 93/00095, Blackburn, et al. WO 95104057, Egbertson, et al, EP 0 478 328, Sugihara, et al. EP 529,858, Porter, et al., EP 0 542 363, and Fisher, et al., EP 0 635 492 disclose certain compounds that are useful for inhibiting the fibrinogen receptor. It has now been discovered that certain compounds are potent inhibitors of the vitronectin receptor. In particular, it has been discovered that such compounds are more potent inhibitors of the vitronectin receptor than the fibrinogen receptor.

SUMMARY OF THE INVENTION

This invention comprises compounds of the formula (1) as described hereinafter, which have pharmacological activity for the inhibition of the vitronection receptor and are useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (1) and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. The novel compounds comprise a benzocycloheptenyl core in which a nitrogen-containing substituent is present on the aromatic six-membered ring of the benzocycloheptene and an aliphatic substituent containing an acidic moiety is present on the seven-membered ring of the benzocycloheptene. The benzocycloheptene ring system is believed to interact favorably with the vitronectin receptor and to orient the substituent sidechains on the six and seven membered rings so that they may also interact favorably with the receptor. It is preferred that about fourteen intervening covalent bonds via the shortest intramolecular path will exist between the acidic group on the aliphatic substituent of the seven-membered ring of the benzocycloheptene and the nitrogen of the nitrogen-containing substituent on the aromatic six-membered ring of the benzocycloheptene.

This invention comprises compounds of formula (I):

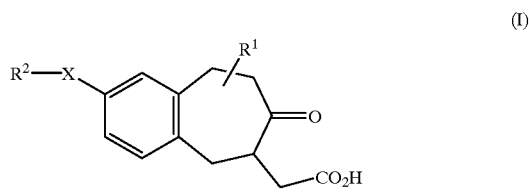

(I)

wherein:
$R^1$ is $R^7$, or A-$C_{0-4}$alkyl, A-$C_{2-4}$alkenyl, A-$C_{2-4}$alkynyl, A-$C_{3-4}$oxoalkenyl, A-$C_{3-4}$oxoalkynyl, A-$C_{1-4}$aminoalkyl, A-$C_{3\ 4}$aminoalkenyl, A-$C_{3-4}$aminoalkynyl, optionally substituted by any accessible combination of one or more of $R^{10}$ or $R^7$;

X is O, C(O)NR', or NR'C(O);
A is H, $C_{3-6}$cycloalkyl, Het or Ar;
$R^7$ is —$COR^8$, —$COCR'_2R^9$, —$C(S)R^8$, —$S(O)_mOR'$, —$S(O)_mNR'R''$, —$PO(OR')$, —$PO(OR')_2$, —$B(OR')_2$, —$NO_2$, or tetrazolyl;
each $R^8$ independently is —OR', —NR'R", —$NR'SO_2R'$, —NR'OR', or —$OCR'_2CO(O)R'$;
$R^9$ is —OR', —CN, —$S(O)_rR'$, —$S(O)_mNR'_2$, —C(O)R', C(O)NR'$_2$, or —$CO_2R'$;
$R^{10}$ is H, halo, —$OR^{11}$, —CN, —$NR'R^{11}$, —$NO_2$, —$CF_3$, $CF_3S(O)_r$—, —$CO_2R'$, —$CONR'_2$, A-$C_{0-6}$alkyl-, A-$C_{1-6}$oxoalkyl-, A-$C_{2-6}$alkenyl-, A-$C_{2-6}$alkynyl-, A-$C_{0-6}$alkyloxy-, A-$C_{0-6}$alkylamino- or A-$C_{0-6}$alkyl-$S(O)_r$—;

$R^{11}$ is R', —C(O)R', —C(O)NR'$_2$, —C(O)OR', —S(O)$_m$R', or —S(O)$_m$NR'$_2$;

$R^2$ is

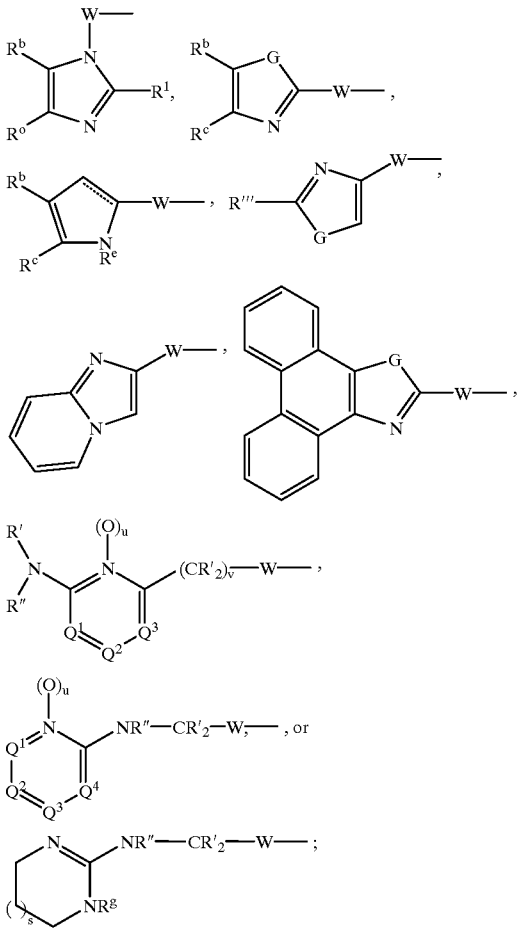

W is —(CHR$^g$)$_a$—U—(CHR$^g$)$_b$—;

U is absent or CO, CR$^g_2$, C(=CR$^g_2$), S(O)$_k$, O, NR$^g$, CR$^g$OR$^g$, CR$^g$(OR$^k$)CR$^g_2$, CR$^g_2$CR$^g$(OR$^k$), C(O)CR$^g_2$, CR$^g_2$C(O), C(O)NR$^1$, NR$^1$C(O), C(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g_2$, NR$^g$CR$^g_2$, CR$^g_2$O, OCR$^g_2$, C≡C or CR$^g$=CR$^g$;

G is NR$^e$, S or O;

R$^g$ is H, C$_{1-6}$alkyl Het-C$_{0-6}$alkyl, C$_{3-7}$cycloalkyl-C$_{0-6}$alkyl or Ar-C$_{0-6}$alkyl;

R$^k$ is R$^g$, —C(O)R$^g$, or —C(O)OR$^f$;

R$^i$ is is H, C$_{1-6}$alkyl, Het-C$_{0-6}$alkyl, C$_{3-7}$cycloalkyl-C$_{0-6}$alkyl, Ar-C$_{0-6}$alkyl, or C$_{1-6}$alkyl substituted by one to three groups chosen from halogen, CN, NR$^g_2$, OR$^g$, SR$^g$, CO$_2$R$^g$, and CON(R$^g$)$_2$;

R$^f$ is H, C$_{1-6}$alkyl or Ar-C$_{1-6}$alkyl;

R$^e$ is H, C$_{1-6}$alkyl, Ar-C$_{1-6}$alkyl, Het-C$_{1-6}$alkyl, C$_{3-7}$cycloalkyl-C$_{1-6}$alkyl, or (CH$_2$)$_k$CO$_2$R$^f$;

R$^b$ and R$^c$ are independently selected from H, C$_{1-6}$alkyl, Ar-C$_{0-6}$alkyl, Het-C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic or heterocyclic ring, optionally substituted by up to three substituents chosen from halogen, CF$_3$, C$_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy;

$Q^1$, $Q^2$, $Q^3$ and $Q^4$ are independently N or C—R$^y$, provided that no more than one of $Q^1$, $Q^2$, $Q^3$ and $Q^4$ is N;

R' is H, C$_{1-6}$alkyl, Ar-C$_{0-6}$alkyl or C$_{3-6}$cycloalkyl-C$_{0-6}$alkyl;

R'' is R', —C(O)R' or —C(O)OR';

R''' is H, C$_{1-6}$alkyl, Ar-C$_{0-6}$alkyl, Het-C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$;

R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g_2$, or C$_{1-6}$alkyl optionally substituted by halo, —OR$^g$, —SR$^g$, —CN, —NR$^g$R'', —NO$_2$, —CF$_3$, R'S(O)$_r$—, —CO$_2$R$^g$, —COR$^g$ or —CONR$^g_2$;

a is 0, 1 or 2;
b is 0, 1 or 2;
k is 0, 1 or 2;
m is 1 or 2;
r is 0, 1 or 2;
s is 0, 1 or 2;
u is 0 or 1; and
v is 0 or 1;

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

and

and each tautomeric form is contemplated as being included within this invention whether existing in equilibrium or locked in one form by appropriate substitution with R'.

The compounds of formula (I) inhibit the binding of vitronectin and other RGD-containing peptides to the vitronectin ($\alpha_v\beta_3$) receptor. Inhibition of the vitronectin receptor on osteoclasts inhibits osteoclastic bone resorption and is useful in the treatment of diseases wherein bone resorption is associated with pathology, such as osteoporosis and osteoarthritis. Additionally, since the compounds of the instant invention inhibit vitronectin receptors on a number of different types of cells, said compounds would be useful in the treatment of inflammatory disorders, such as rheumatoid arthritis and psoriasis, and cardiovascular diseases, such as atherosclerosis and restenosis. The compounds of Formula (I) of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compounds of the present invention may also be useful for wound healing.

In particular, the compounds of the present invention are useful for the treatment, including prevention, of angiogenic disorders. The term "angiogenic disorders" as used herein includes conditions involving abnormal neovascularization. Where the growth of new blood vessels is the cause of, or contributes to, the pathology associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus, the compounds of the present invention inhibit tumor tissue angiogenesis, thereby preventing tumor metastasis and tumor growth.

Thus, according to the methods of the present invention, the inhibition of angiogenesis using the compounds of the present invention can ameliorate the symptoms of the disease, and, in some cases, can cure the disease.

A preferred therapeutic target for the compounds of the instant invention are eye diseases chacterized by neovascularization. Such eye diseases include corneal neovascular disorders, such as corneal transplantation, herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

With respect to formula (I):

Preferably, X is O.

Suitably $R^2$ is

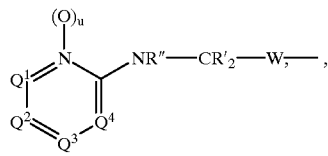

wherein $Q^1$, $Q^2$, and $Q^3$ are each $CR^y$, $Q^4$ is $CR^y$ or N and u is 0, and preferably, each R' is H, R" is H, $C_{1-6}$alkyl, —C(O)$C_{1-6}$alkyl, C(O)O$C_{1-6}$alkyl, —C(O)$C_{0-6}$alkyl-Ar, or C(O)O$C_{0-6}$alkyl-Ar, W is —CH$_2$—CH$_2$—, and $R^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$—CONR$^g{}_2$, or $C_{1-6}$alkyl.

Alternately $R^2$ is

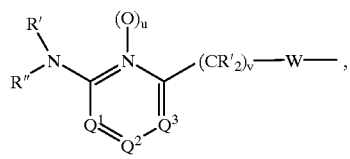

wherein $Q^1$, $Q^2$, and $Q^3$ are each CH and u is 0, and preferably, each R' is H, R" is H or $C_{1-4}$alkyl and W is —CH$_2$—CH$_2$—.

Alternately $R^2$ is

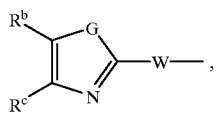

wherein G is NH and $R^b$ and $R^c$ are each H. and preferably, W is —NR$^9$—(CHR$^g$)$_b$—.

Alternately $R^2$ is

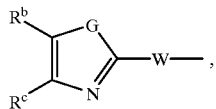

wherein G is NH and $R^b$ and $R^c$ are joined together to form a five or six membered aromatic or non-aromatic carbocyclic or heterocyclic ring, optionally substituted by up to three substituents chosen from halogen, CF$_3$, $C_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy. Preferably, $R^b$ and $R^c$ are joined together to form a six membered aromatic carbocyclic or heterocyclic ring and W is —CH$_2$—CH$_2$—.

Alternately $R^2$ is

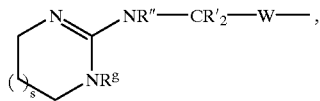

wherein each R' is H, R" is H or $C_{1-4}$alkyl, $R^g$ is H or $C_{1-4}$alkyl and s 0, 1 or 2 and, preferably, W is —CH$_2$—CH$_2$—.

With respect to formula (1), suitably $R^1$ is H, $C_{1-6}$alkyl, Ar-$C_{0-6}$alkyl, Het-$C_{0-6}$alkyl, or $C_{3-6}$cycloalkyl-$C_{0-6}$alkyl, —(CH$_2$)$_{1-2}$COR$^8$, —(CH$_2$)$_2$OR', and CH$_2$CF$_3$. Preferably, $R^1$ is H, $C_{1-4}$alkyl, Ph-$C_{0-6}$alkyl, —(CH$_2$)$_{1-2}$COOR', —(CH$_2$)$_2$OR', and CH$_2$CF$_3$, in which R' is H or $C_{1-4}$alkyl.

Representative of the novel compounds of this invention is (±)-2-(2-pyridylamino)propoxy-6,78,9-tetrahydro-7-oxo-5H-benzocycloheptenyl-6-acetic acid or a pharmaceutically acceptable salt thereof.

In cases wherein the compounds of this invention may have one or more chiral centers, unless specified this invention includes each unique nonracemic compound which may be synthesized and resolved by conventional techniques. In cases in which compounds have unsaturated carbon-carbon double bonds, both the cis (Z) and trans (E) isomers are within the scope of this invention. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo. Thus, in another aspect of this invention are novel prodrugs, which are also intermediates in the preparation of formula (I) compounds, of formula (II):

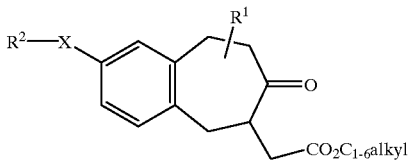

(II)

wherein:

$R^1$ is $R^7$, or A-$C_{0-4}$alkyl, A-$C_{2-4}$alkenyl, A-$C_{2-4}$alkynyl, A-$C_{3-4}$oxoalkenyl, A-$C_{3-4}$oxoalkynyl, A-$C_{1-4}$aminoalkyl, A-$C_{3-4}$aminoalkenyl, A-$C_{3-4}$aminoalkynyl, optionally substituted by any accessible combination of one or more of $R^1O$ or $R^7$;

X is O, C(O)NR', or NR'C(O);

A is H, $C_{3-6}$cycloalkyl, Het or Ar;

$R^7$ is —$COR^8$, —$COCR'_2R^9$, —C(S)$R^8$, —S(O)$_m$OR', —S(O)$_m$NR'R", —PO(OR'), —PO(OR')$_2$, —B(OR')$_2$, —NO$_2$, or tetrazolyl;

each $R^8$ independently is —OR', —NR'R", —NR'SO$_2$R', —NR'OR', or —OCR'$_2$CO(O)R';

$R^9$ is —OR', —CN, —S(O)$_r$R', —S(O)$_m$NR'$_2$, —C(O)R', C(O)NR'$_2$, or —CO$_2$R';

$R^{10}$ is H, halo, —OR$^{11}$, —CN, —NR'R$^{11}$, —NO$_2$, —CF$_3$, CF$_3$S(O)$_r$—, —CO$_2$R', —CONR'$_2$, A-$C_{0-6}$alkyl-, A-$C_{1-6}$oxoalkyl-, A-$C_{2-6}$alkenyl-, A-$C_{2-6}$alkynyl-, A-$C_{0-6}$alkyloxy-, A-$C_{0-6}$alkylamino- or A-$C_{0-6}$alkyl-S(O)$_r$-;

$R^{11}$ is R', —C(O)R', —C(O)NR'$_2$, —C(O)OR', —S(O)$_m$R', or —S(O)$_m$NR'$_2$;

$R^2$ is

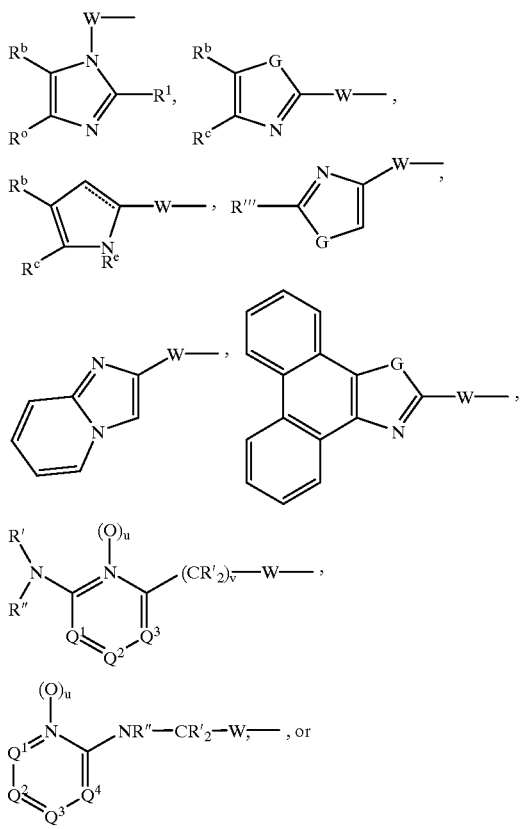

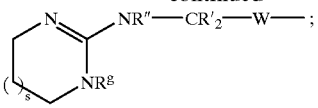

W is —(CHR$^g$)$_a$—U—(CHR$^g$)$_b$—;

U is absent or CO, CR$^g_2$, C(=CR$^g_2$), S(O)$^k$, O, NR$^g$, CR$^g$OR$^g$, CR$^g$(OR$^k$)CR$^g_2$, CR$^g_2$CR$^g$(OR$^k$), C(O)CR$^g_2$, CR$^g_2$C(O), CONR$^i$ N R$^i$ CO OC(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g_2$, NR$^g$CR$^g_2$, CR$^g_2$O, OCR$^g_2$, C≡C or CR$^g$=CR$^g$;

G is NR$^e$, S or O;

$R^g$ is H, $C_{1-6}$alkyl, Het-$C_{0-6}$alkyl, $C_{3-7}$cycloalkyl-$C_{0-6}$alkyl or Ar-$C_{0-6}$alkyl;

$R^k$ is $R^g$, —C(O)R$^g$, or —C(O)OR$^f$;

$R^i$ is H, $C_{1-6}$alkyl, Het-$C_{0-6}$alkyl, $C_{3-7}$cycloalkyl-$C_{0-6}$alkyl, Ar-$C_{0-6}$alkyl, or $C_{1-6}$alkyl substituted by one to three groups chosen from halogen, CN, NR$^g_2$, OR$^g$, SR$^g$, CO$_2$R$^g$, and CON(R$^g$)$_2$;

$R^f$ is H, $C_{1-6}$alkyl or Ar-$C_{1-6}$alkyl;

$R^e$ is H, $C_{1-6}$alkyl, Ar-$C_{1-6}$alkyl, Het-$C_{1-6}$alkyl, $C_{3-7}$cycloalkyl-$C_{1-6}$alkyl, or (CH$_2$)$_k$CO$_2$R$^g$;

$R^b$ and $R^c$ are independently selected from H, $C_{1-6}$alkyl, Ar-$C_{0-6}$alkyl, Het-$C_{0-6}$alkyl, or $C_{3-6}$cycloalkyl-$C_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or $R^b$ and $R^c$ are joined together to form a five or six membered aromatic or non-aromatic carbocyclic or heterocyclic ring, optionally substituted by up to three substituents chosen from halogen, CF$_3$, $C_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy;

$Q^1$, $Q^2$, $Q^3$ and $Q^4$ are independently N or C—R$^y$, provided that no more than one of $Q^1$, $Q^2$, $Q^3$ and $Q^4$ is N;

R' is H, $C_{1-6}$alkyl, Ar-$C_{0-6}$alkyl or $C_{3-6}$cycloalkyl-$C_{0-6}$alkyl;

R" is R', —C(O)R' or —C(O)OR';

R''' is H, $C_{1-6}$alkyl, Ar-$C_{0-6}$alkyl, Het-$C_{0-6}$alkyl, or $C_{3-6}$cycloalkyl-$C_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$;

$R^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g_2$, or $C_{1-6}$alkyl optionally substituted by halo, —OR$^g$, —SR$^g$, —CN, —NR$^g$R", —NO$_2$, —CF$_3$, R'S(O)$_r$—, —CO$_2$R$^g$, —COR$^g$ or —CONR$^g_2$;

a is 0, 1 or 2;
b is 0, 1 or 2;
k is 0, 1 or 2;
m is 1 or 2;
r is 0, 1 or 2;
s is 0, 1 or 2;
u is 0 or 1; and
v is 0 or 1;

or a pharmaceutically acceptable salt thereof.

Preferably, X is O and $R^2$ is

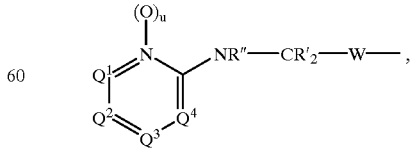

wherein $Q^1$, $Q^2$, and $Q^3$ are each CR$^y$, $Q^4$ is CR$^y$ or N and u is 0, and preferably, each R' is H, R" is H, $C_{1-6}$alkyl, —C(O)$C_{1-6}$alkyl, C(O)O$C_{1-6}$alkyl, —C(O)$C_{0-6}$alkyl-Ar, or C(O)OC$_{0-6}$alkyl-Ar, W is —CH$_2$—CH$_2$—, and R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$, —CONR$^g$$_2$, or C$_{1-6}$alkyl.

Representative of the novel prodrugs of this invention is methyl (±)-2-(2-pyridylamino)propoxy-6,7,8,9-tetrahydro-7-oxo-5H-benzocycloheptenyl-6-acetate or a pharmaceutically acceptable salt thereof.

In yet another aspect of this invention are novel intermediates of formula (III):

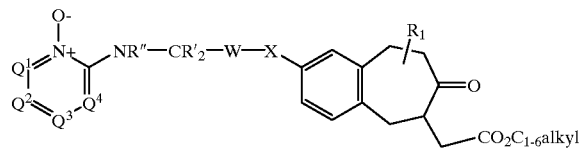

(III)

R$^1$ is R$^7$, or A-C$_{0-4}$alkyl, A-C$_{2-4}$alkenyl, A-C$_{2-4}$alkynyl, A-C$_{3-4}$oxoalkenyl, A-C$_{3-4}$oxoalkynyl, A-C$_{1-4}$aminoalkyl, A-C$_{3-4}$aminoalkenyl, A-C$_{3-4}$aminoalkynyl, optionally substituted by any accessible combination of one or more of R$^{10}$ or R$^7$;

X is O, C(O)NR', or NR'C(O);

A is H, C$_{3-6}$cycloalkyl, Het or Ar;

R$^7$ is —COR$^8$, —COCR'$_2$R$^9$, —C(S)R$^8$, —S(O)$_m$OR', —S(O)$_m$NR'R", —PO(OR'), —PO(OR')$_2$, —B(OR')$_2$, —NO$_2$, or tetrazolyl;

each R$^8$ independently is —OR', —NR'R", —NR'SO$_2$R', —NR'OR', or —OCR'$_2$CO(O)R';

R$^9$ is —OR', —CN, —S(O)$_r$R', —S(O)$_m$NR'$_2$, —C(O)R', C(O)NR'$_2$, or —CO$_2$R';

R$^{10}$ is H, halo, —OR$^{11}$, —CN, —NR'R$^{11}$, —NO$_2$, —CF$_3$, CF$_3$S(O)$_r$—, —CO$_2$R', —CONR'$_2$, A-C$_{0-6}$alkyl-, A-C$_{1-6}$ oxoalkyl-, A-C$_{2-6}$alkenyl-, A-C$_{2-6}$alkynyl-, A-C$_{0-6}$ alkyloxy-, A-C$_{0-6}$alkylamino- or A-C$_{0-6}$alkyl-S(O)$_r$-;

R$^{11}$ is R', —C(O)R', —C(O)NR'$_2$, —C(O)OR', —S(O)$_m$R', or —S(O)$_m$NR'$_2$;

W is —(CHR$^g$)$_a$—U—(CHR$^g$)$_b$—;

U is absent or CO, CR$^g$$_2$, C(=CR$^g$$_2$), S(O)$_k$, O, NR$^g$, CR$^g$OR$^g$, CR$^g$(OR$^k$)CR$^g$$_2$, CR$^g$$_2$CR$^g$(OR$^k$), C(O)CR$^g$$_2$, CR$^g$$_2$C(O), CON R$^i$ N R$^i$ CO OC(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g$$_2$, NR$^g$CR$^g$$_2$, CR$^g$$_2$O, OCR$^g$$_2$, C≡C or CR$^g$=CR$^g$;

R$^g$ is H, C$_{1-6}$alkyl, Het-C$_{0-6}$alkyl, C$_{3-7}$cycloalkyl-C$_{0-6}$ alkyl or Ar-C$_{0-6}$alkyl;

R$^k$ is R$^g$, —C(O)R$^g$, or —C(O)OR$^f$;

R$^i$ is is H, C$_{1-6}$alkyl, Het-C$_{0-6}$alkyl, C$_{3-7}$cycloalkyl-C$_{0-6}$ alkyl, Ar-C$_{0-6}$alkyl, or C$_{1-6}$alkyl substituted by one to three groups chosen from halogen, CN, NR$^g$$_2$, OR$^g$, SR$^g$, CO$_2$R$^g$, and CON(R$^g$)$_2$;

R$^f$ is H, C$_{1-6}$alkyl or Ar-C$_{1-6}$alkyl;

Q$^1$, Q$^2$, Q$^3$ and Q$^4$ are independently N or C—R$^y$, provided that no more than one of Q$^1$, Q$^2$, Q$^3$ and Q$^4$ is N;

R' is H, C$_{1-6}$alkyl, Ar-C$_{0-6}$alkyl or C$_{3-6}$cycloalkyl-C$_{0-6}$alkyl;

R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g$$_2$, or C$_{1-6}$alkyl optionally substituted by halo, —OR$^g$, —SR$^g$, —CN, —NR$^g$R", —NO$_2$, —CF$_3$, R'S(O)$_r$—, —CO$_2$R$^g$, —COR$^g$ or —CONR$^g$$_2$;

a is 0, 1 or 2;

b is 0, 1 or 2;

m is 1 or 2; and r is 0, 1 or 2;

or a pharmaceutically acceptable salt thereof.

Preferably, X is O and Q$^1$, Q$^2$, and Q$^3$ are each CR$^y$, Q$^4$ is CR$^y$ or N, and preferably, each R' is H, R" is H, C$_{1-6}$alkyl, —C(O)C$_{1-6}$alkyl, C(O)OC$_{1-6}$alkyl, —C(O)C$_{0-6}$alkyl-Ar, or C(O)OC$_{0-6}$alkyl-Ar, W is —CH$_2$—CH$_2$—, and R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$—CONR$^g$$_2$, or C$_{1-6}$alkyl.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

C$_{1-4}$alkyl as applied herein means an optionally substituted alkyl group of 1 to 4 carbon atoms, and includes methyl, ethyl, n-propyl, isopropyl, n-butyl, isobutyl and t-butyl. C$_{1-6}$alkyl additionally includes pentyl, n-pentyl, isopentyl, neopentyl and hexyl and the simple aliphatic isomers thereof. C$_{0-4}$alkyl and C$_{0-6}$alkyl additionally indicates that no alkyl group need be present (e.g., that a covalent bond is present).

Any C$_{1-4}$alkyl or C$_{1-6}$ alkyl, C$_{2-6}$ alkenyl, C$_{2-6}$ alkynyl or C$_{1-6}$ oxoalkyl may be optionally substituted with the group R$^x$, which may be on any carbon atom that results in a stable structure and is available by conventional synthetic techniques. Suitable groups for R$^x$ are C$_{1-4}$alkyl, OR', SR', C$_{1-4}$alkylsulfonyl, C$_{1-4}$alkylsulfoxyl, —CN, N(R')$_2$, CH$_2$N(R')$_2$, —NO$_2$, —CF$_3$, —CO$_2$R'—CON(R')$_2$, —COR', —NR'C(O)R', F, Cl, Br, I, or CF$_3$S(O)$_r$—,wherein r is 0, 1 or 2.

Ar, or aryl, as applied herein, means phenyl or naphthyl, or phenyl or naphthyl substituted by one to three substituents, such as those defined above for alkyl, especially C$_{1-4}$alkyl, C$_{1-4}$alkoxy, C$_{1-4}$alkthio, CF$_3$, NH$_2$, OH, F, Cl, Br or L.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydroquinoline and isoquinoline. Any accessible combination of up to three substituents on the Het ring, such as those defined above for alkyl that are available by chemical synthesis and are stable are within the scope of this invention.

C$_{3-7}$cycloalkyl refers to an optionally substituted carbocyclic system of three to seven carbon atoms, which may contain up to two unsaturated carbon-carbon bonds. Typical of C$_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

When R$^b$ and R$^c$ are joined together to form a five- or six-membered aromatic or non-aromatic carbocyclic or heterocyclic ring fused to the ring to which R$^b$ and R$^c$ are attached, the ring formed will generally be a five- or six-membered heterocycle selected from those listed above for Het, or will be a phenyl, cyclohexyl or cyclopentyl ring. Preferably R$^b$ and R$^c$ will be -D1=D2-D3=D4 wherein D1–D4 are independently CH, N or C—R$_x$ with the proviso that no more than two of D1–D4 are N. Most preferably, when R$^b$ and R$^c$ are joined together they form the group —CH=CH—CH=CH—.

Certain radical groups are abbreviated herein, t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to 1-(3-dimethyiaminopropyl)-3-ethylcarbodiimide, hydrochloride. HOBt refers to 1-hydroxybenzotriazole, THF refers to tetrahydrofuran, DIEA refers to diisopropylethylamine, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

Compounds of the formula (I) are prepared by the methods described in Schemes I–IV and by methods analogous to those described in these schemes.

Scheme I

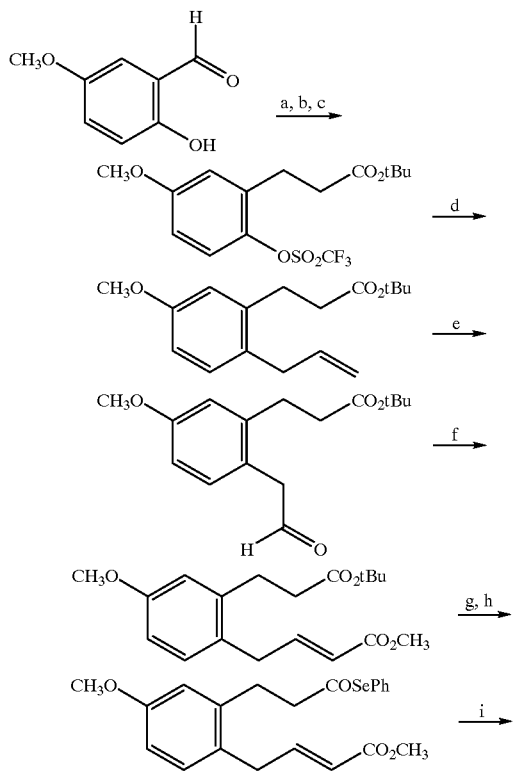

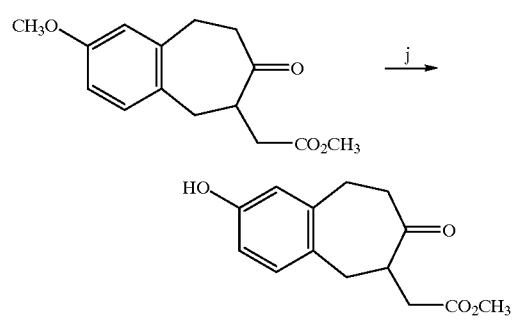

a) $Ph_3P = CHCO_2tBu/PhCH_3$
b) $H_2/Pd/C$;
c) $(CF_3SO_2)_2O/Pyridine$;
d) $Bu_3SnCH_2CH = CH_2/LiCl/(Ph_3P)_2PdCl_2/DMF$;
e) 4% $OsO_4/H_2O/Na_2CO_3$;
f) $Ph_3P = CHCO_2CH_3/PhCH_3$;
g) $TFA/CH_2Cl_2$;
h) $Ph_3P/PhthSePh$;
i) $AIBN/PhCH_3$;
j) $AlCl_3/Et_2S/CH_2Cl_2$;

Scheme-II

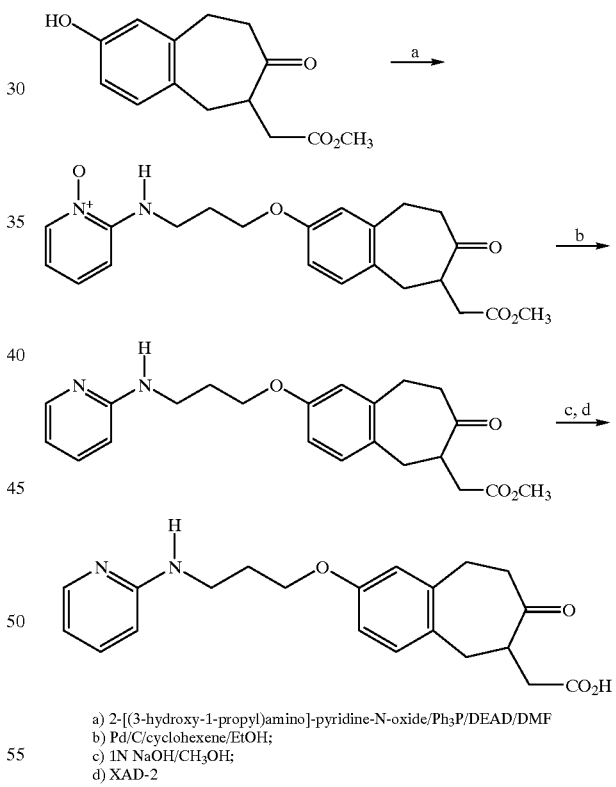

a) 2-[(3-hydroxy-1-propyl)amino]-pyridine-N-oxide/$Ph_3P$/DEAD/DMF
b) Pd/C/cyclohexene/EtOH;
c) 1N NaOH/$CH_3OH$;
d) XAD-2

Scheme-III

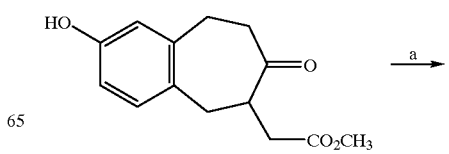

13

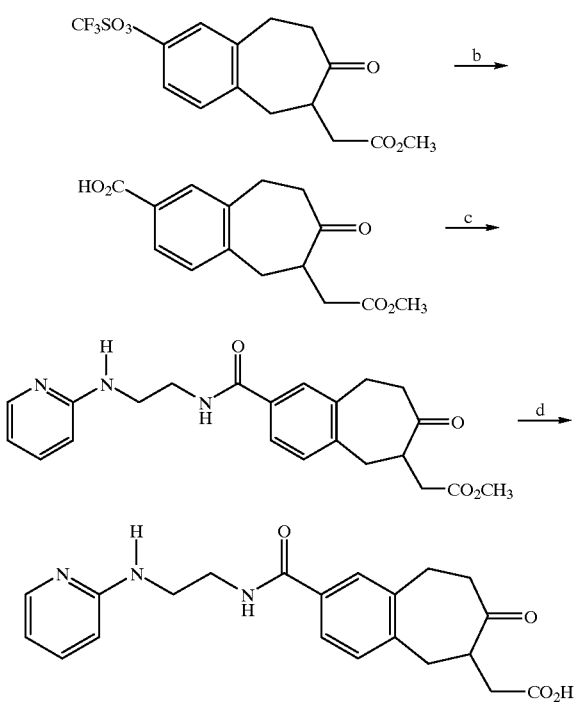

a) Tf₂O/pyridine;
b) CO/KOAc/Pd(OAc)₂/dppf/DMSO;
c) 2-[(2-amino-1-ethyl)amino]pyridine/EDC/HOBt•H₂O/(i-Pr)₂NEt/CH₃CN;
d) 1.0 N NaOH/MeOH.

Scheme-IV

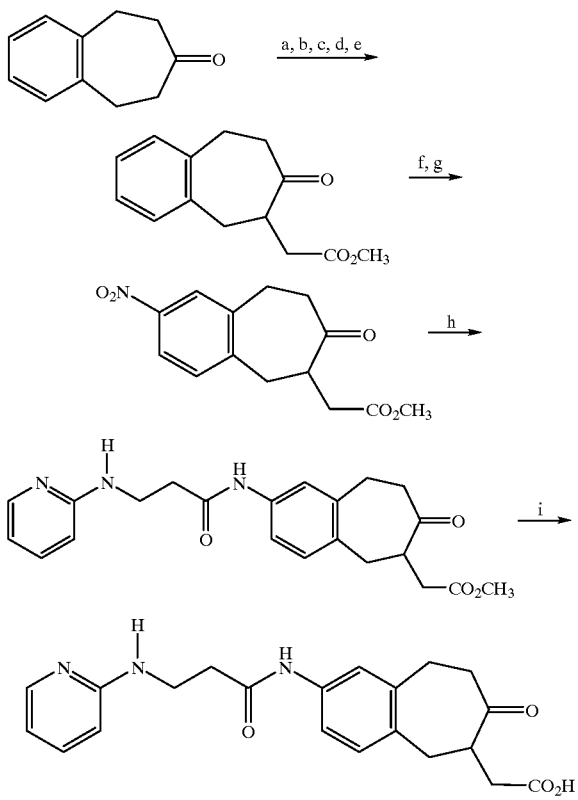

14 a) tBuMe₂SiOTf/TEA;
b) O₃/Me₂S;
c) Ph₃P = CHCO₂Me/H₃O⁺;
d) Ph₃P/PhthSePh;
e) AIBN/PhCH₃;
f) HNO₃/HOAc;
g) H₂/Pd/C/MeOH;
h) 3-(2-pyridinylamino)propionic acid/EDC/HOBt•H₂O/(i-Pr)₂NEt/CH₃CN;
i) 1.0 N NaOH/MeOH.

The formula (I) compounds of the present invention may also be prepared by methods analogous to those described in Bondinell, et al., PCT application WO 93/00095, published Jan. 7, 1993 and Bondinell, et al., PCT application WO 94/14776, published Jul. 7, 1994. Reference should be made to said patent applications for their full disclosure, particularly to the methods of preparing the compounds therein, said disclosures being incorporated herein by reference.

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.,* 29, 984 (1986) and *J. Med. Chem.,* 30, 2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

Useful intermediates for preparing formula (1) compounds in which $R^2$ is a benzimidazole are disclosed in Nestor et al, *J. Med. Chem.* 1984, 27, 320. Representative methods for preparing benzimidazole compounds useful as intermediates in the present invention are also common to the art and may be found, for instance, in EP-A 0 381 033.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water.

The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, anti-angiogenic, anti-inflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

The compounds may be tested in one of several biological assays to determine the concentration of compound which is required to have a given pharmacological effect.

Inhibition of vitronectin binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 ,g of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 MM $MgCl_2$) to a final compound concentration of 100 $\mu$M. This solution is then diluted to the required final compound concentration. Various concentrations of unlabeled antagonists (0.001–100 $\mu$M) were added to the wells in triplicates, followed by the addition of 5.0 nM of [$^3$H]-SK&F-107260 (65–86 Ci/rnmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 LM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to the equation: $K_i=IC_{50}/(1+L/K_d)$, where L and $K_d$ were the concentration and the dissociation constant of [$^3$H]-SK&F-107260, respectively.

($\pm$)-2-(2-Pyridylamino)propoxy-6,7,8,9-tetrahydro-7-oxo-5H- benzocycloheptenvl-6-acetic acid, a compound of the present invention, inhibits vitronectin binding to SK&F 107260 with a $K_i$ of about 23 nM.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et a., *Cells and Materials* 1991, Sup. 1, 69-74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of $2.5–5.0 \times 10^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5–6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rats, circulating ionized calcium levels are measured in whole blood immediately after it has been withdrawn by tail venipuncture into heparinized tubes. Rats are included if the ionized Ca level (measured with a Ciba-Corning model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1–34 peptide (hPTH1-34, dose 1.25 ug/kg/h in saline/0.1% bovine serum albumin, Bachem, Calif.) or a mixture of hPTH1-34 and test material, by continuous intravenous infusion via the venous catheter using an external syringe pump. The calcemic response of each rat is measured at two-hourly intervals during the infusion period of 6–8 hours.

Human Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitve ELISA.

Assay 1 (Using Laser Confocal Microscopy)

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5 / mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control ($IgG_{2a}$ diluted to 100 ug/ml). The samples are incubated at 37° C. for 30 mins.

0.5ml aliquots of the cells are seeded onto sterile dentine slices in a 48-well plate and incubated at 37° C. for 2 hours. Each treatment is screened in quadruplicate.

The slices are washed in six changes of warm PBS (10 ml /well in a 6-well plate) and then placed into fresh medium containing the compound treatment or control samples. The samples are incubated at 37° C. for 48 hours.

Tartrate Resistant Acid Phosphatase (TRAP) Procedure (Selective Stain for Cells of the Osteoclast Lineage)

The bone slices containing the attached osteoclasts are washed in phosphate buffered saline and fixed in 2% gluteraldehyde (in 0.2M sodium cacodylate) for 5 mins.

They are then washed in water and are incubated for 4 minutes in TRAP buffer at 37° C. (0.5 mg/ml naphthol AS-BI phosphate dissolved in N,N-dimethylformamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/purple precipitate) are enumerated by bright-field microscopy and are then removed from the surface of the dentine by sonication.

Pit volumes are determined using the Nikon/Lasertec ILM21W confocal ,microscope.

Assay 2 (Using an ELISA Readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method desribed above in Assay 1, the compounds are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tissue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His- Asp-Gly-Gly-Arg) that is present in the carboxy-terminal telopeptide of the a1-chain of type I collagen. The results are expressed as % inhibition of resorption compared to a vehicle control.

Human Osteoclast Adhesion Assay

The human osteoclasts are enriched and prepared for compound screening as described above in the inital 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5 ug/ml) and incubated for 2 hours at 37° C.

Non adherent cells are removed by washing the slides vigorously in phosphate buffered saline and the cells remaining on the slides are fixed in acetone.

The osteoclasts are stained for tartrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay

Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Steptomycin.

Constructs and Transfections

A 3.2 kb EcoRI-KpnI fragment of the $\alpha_v$ subunit and a 2.4 kb XbaI-XhoI fragment of the $\beta_3$ subunit were inserted into the EcoRI-EcoRV cloning sites of the pCDN vector (Aiyar et al., 1994 ) which contains a CMV promoter and a G418 selectable marker by blunt end ligation. For stable expression, 80×10$^6$ HEK 293 cells were electrotransformed with $\alpha_v$+$\beta_3$ constructs (20 µg DNA of each subunit) using a Gene Pulser (Hensley et al., 1994 ) and plated in 100 mm plates (5×10$^5$ cells/plate). After 48 hr, the growth medium was supplemented with 450 µg/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 µg/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0. 1% BSA at a density of $0.5 \times 10^6$ cells/mL. 0.1 mL of cell suspension was added to each well and incubated for 1 hr at 37° C., in the presence or absence of various $\alpha_v\beta_3$ antagonists. Following incubation, 0.025 mL of a 10% formaldehyde solution, pH 7.4, was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water. The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

In Vivo Angiogenesis Model

The compounds of the present invention are tested for the inhibition of angiogenesis using the model described in Passaniti, et al., *Laboratory Investigation*, 67: 519–528 (1992).

Inhibition of RGD-Mediated GPIIb-IIIa Binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 rnM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM $CaCl_2$ (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70 C until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 µg/mL polylysine (Sigma Chemical Co., St. Louis, Mo.) at room temperature for 1 h to block nonspecific binding. Various concentrations of unlabeled benzazepines were added to the wells in quadruplicate. [3H]-SK&F-107260 was applied to each well at a final concentration of 4.5 nM, followed by the addition of 1 µg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 µM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: $Ki = IC50/(1+LKd)$, where L is the concentration of [3H]-SK&F-107260 used in the competitive binding assay (4.5 nM), and Kd is the dissociation constant of [3H]-SK&F-107260 which is 4.5 nM as determined by Scatchard analysis.

The examples which follow are intended in no way to limit the scope of this invention, but are provided to illustrate how to make and use the compounds of this invention. Many other embodiments will be readily apparent to those skilled in the art.

EXAMPLES

Nuclear magnetic resonance spectra were recorded at either 250 or 400 MHz using, respectively, a Bruker AM 250 or Bruker AC 400 spectrometer. $CDCl_3$ is deuteriochloroform, DMSO-d$_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet. m=multiplet, dd=doublet of doublets, dt=doublet of triplets, app=apparent, br=broad. J indicates * . the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5μ Apex-ODS indicates an octadecylsilyl derivatized silica gel chromatographic support having a nominal particle size of 5 μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo.

Example 1

Preparation of methyl (±)-2-hydroxy-6,7,8,9-tetrahydro-7-oxo-5H-benzocycloheptenyl-6-acetate a) tert Butyl 2-hydroxy-5-methoxycinnamate A mixture of 2-hydroxy-5-methoxybenzaldehyde (19 g, 0.125 mol) and (tert-butoxycarbonylmethylene) tripheylphosphorane (50 g, 0.133 mol) in toluene (150 mL) was heated at 90° C. for 2.5 h and concentrated. The titlted compound (27.5 g)was obtained after passing through a short $SiO_2$ column using 18% EtOAc/hexane.

b) tert-Butyl 3-(2-hydroxy-5-methoxyphenyl)propionate

A mixture of tert-butyl 2-hydroxy-5-methoxycinnamate (27.5 g, 0.11 mol) and 10% Pd/C (2.6 g) in MeOH (350 mL) under H. pressure (45 psi) was shaken for 8 h and filtered. The filtrate was concentrated to to the titled compound (27 g).

c) tert-Butyl 3-(2-trifluoromethylsulfonyloxy-5-methoxyphenyl)propionate

To a solution of tert-butyl 3-(2-hydroxy-5-methoxyphenyl)propionate (17.7 g, 0.070 mol) in dry pyridine (100 mL) at 0° C. was added dropwise triflic anhydride (20 g, 0.071 mmol). After 4 h the mixture was diluted with ether and washed with water, dried ($MgSO_4$) and evaporated. The titled compound (18.2 g, 67%) was obtained by passing through a short $SiO_2$ column using 10% EtOAc/hexane.

d) tert-Butyl 3-(2-propeny-5-methoxyphenyl)propionate

Argon was passed through a solution of tert-butyl 3-(2-trifluoromethylsulfonyloxy-5-methoxyphenyl)propionate (15 g, 39 mmol), allyltributyl tin (15.8 mL, 51 mmol), and lithium chloride (2.1 g, 51 mmol) in DMF (120 mL) for 10 min, and bis(triphenylphosphine)palladium dchloride (1.5 g, 2.2 mmol) was added. The reaction mixture was heated at 95° C. for 1.5 h and evaporated. The residue was partitioned between 10% KF aqoues solution and ether. The combined extracts were dried and evaporated to give the titled compound (18.5 g).

e) tert-Butyl 3-(2-oxoethyl-5-methoxyphenyl)propionate

To a solution of tert-butyl 3-(2-propeny-5-methoxyphenyl)propionate (7.2 g, 26 mmol) in THF (60 mL) and $H_2O$ (30 mL) were added $NaO_4$ (9.8 g, 46 nmmol) and 4% osmium tetroxide (1 mL). After stirring at RT, the mixture was filtered and the filtrate was diluted with ether. The combined extracts were dried and evaporated to give the crude product which was flash chromatographed to give the titled compound (3.0 g; 43% yield).

f) tert-Butyl 4-[2-[(2-carboxy)ethyl]-5-methoxyphenyl]-2-butenoate

A mixture of tert-butyl 3-(2-oxoethyl-5-methoxyphenyl) propionate (3 g, 10.8 mmol) and methyl (triphenylphosphoranylidene)acetate (4 g, 12 mmol) in toluene (75 mL) was heated at 90° C. for 2.5 h and concentrated. The titited compound (3.1 g, 86%) was obtained after flash column chromatography ($SiO_2/CH_2Cl_2$).

g) Methyl 4-[2-[(2-carboxy)ethyl]-5-methoxyphenyl]-2-butenoate

A mixture of methyl 4-[2-[(2-tert-butoxycarboxy)ethyl]-5-methoxyphenyl]-2-butenoate (2.1 g, 6.3 mmol), and 4M HCl in dioxane (10 mL) in $CH_2Cl_2$ (75 mL) was stirred at RT for 4.5 h and evaporated to give the titled compound (1.4 g, 80% yield).

h) Methyl 4-[2-[(3-oxo-3-(phenylseleno)propyl]-5-methoxyphenyl]-2-butenoate

To a solution of methyl 4-[2-[(2-carboxy)ethyl]-5-methoxyphenyl]-2-butenoate (2.8 g, 10 mmol) in anhydrous $CH_2Cl_2$ (25 mL) at −40° C. was added dropwise $Bu_3P$ (4.5 mL, 18 mmol), followed by N-phenylselenophthalimide (4.2 g, 14 mmol). The mixture was warmed to RT and the suspension was filtered after 1.5 h. The filtrate was concentrated and flash chromatographed ($SiO_2$/5–7 %EtOAc/hexane eluant) to give 1.9 g of the titled compound in 38% yield.

i) Methyl (±)-2-methoxy-6,7,8,9-tetrahydro-7-oxo-5H-benzocycloheptenyl-6-acetate A solution of methyl 4-[2-[(3-oxo-3-(phenylseleno) propyl]-5- methoxyphenyl]-2-butenoate (1.45 g, 3.5 mmol) and AIBN (32 mg) in dry benzene (320 mL) was warmed to reflux at 95° C. and treated dropwise over 2 h using syringe pump with a solution of $Bu_3SnH$ 1.2 mL, 4.2 mmol, 1.2 equiv) in benzene (20 miL). After an additional 0.5 h at reflux, the mixture was cooled and concentrated. Flash chromatography ($SiO_2$/8–12% EtOAc/hexane eluant) gave 0.88 g (76% yield)of the titled compound.

j) Methyl (±)-2-hydroxy-6,7,8,9-tetrahydro-7-oxo-5H-benzocycloheptenyl-6-acetate To a solution of diethylsulfide (0.73 g, 8.16 mmol) in anhydrous $CH_2Cl_2$ (50 mL) at −40° C. was added dropwise $AlCl_3$ (1.08 g, 8.16 mmol) at 0° C. The resulting mixture was warmed to RT and a solution of methyl (±)-2-methoxy-6,7,8,9-tetrahydro-7-oxo-5H-benzocycloheptenyl-6-acetate (180 mg, 0.68 mmol) in $CH_2Cl_2$ (12 mL) was added. After 1 h the mixture was diluted with ice-cold 1N HCl solution, extracted with $CH_2Cl_2$. The combined extracts were dried and evaporated. Flash chromatography ($SiO_2$/0.5–0.8% MeOH/ $CH_2Cl_2$ eluant) gave 124 mg (89% yield) of the titled compound.

Example 2

Preparation of (±)-2-(2-Pyridylamino)propoxy-6,7,8,9-tetrahydro-7-oxo-5H-benzocycloheptenyl-6-acetic acid a) Methyl (±)-2-[2-(N-oxopyridyl)amino]propoxy-2- 6,7,8,9-tetrahydro-7-oxo-5H-benzocycloheptenyl-6-acetate A solution of 2-[(3-hydroxy-1-propyl)amino]pyridine-N-oxide (252 mg, 1.5 mmol, 3 equiv) and diethyl azodicarboxylate (0.22 mL, 1.4 mmol) in anhydrous DMF (12 mL) was added dropwise over 10 min to a solution of methyl (±)-2-hydroxy-6,7,8,9-tetrahydro-7-oxo-5H-benzocycloheptenyl-6-acetate (124 mg, 0.5 mmol) and triphenylphosphine (432 mg, 1.65 mmol, 2.7 equiv) in anhydrous DMF (5 mL) at RT under argon. After 24 h, the reaction was concentrated on the rotavap, and the residue was reconcentrated from xylenes to remove residual DMF. Silica gel chromatography (30% EtOAc/hexanes (0.5 L), then EtOAc (1 L), then 5% $MeOH/CHCl_3$) gave the title compound (120 mg, 60 %). $^1H$ NMR (400 MHz, $CDCl_3$) δ 8.10 (dd, J=6.6, 1.3 Hz, 1H), 7.15 (m, 1H), 7.10 (d, J=2.6 Hz, 1H),7.02 (m, 1H), 6.80 (d, J=2.6 Hz, 1H), 6.75 (dd, J=8.2, 2.6 Hz, 1H), 6.64 (d, J=2.6 Hz, 1H), 6.55 (dd, J =8.5, 1.6 Hz, 1H), 4.80 (m,1H), 4.10 (m, 2H), 3.68 (s, 3H), 3.50 (m, 2H), 3.05 (m, 1H), 2.65–2.95 (m, 6H), 2.55 (m,1H), 2.35 (dd, J=15.6, 9.4 Hz, 1H), 2.10–2.20 (m, 2H); MS (ES) m/e 399.2 $(M+H)^+$.

b) Methyl (±)-2-(2-pyridylamino)propoxy-6,7,8,9-tetrahydro-7-oxo-5H-benzocycloheptenyl-6-acetate A mixture of methyl (±)-2-[2-(N-oxopyridyl)amino]propoxy-2-6,7,8,9-tetrahydro-7-oxo-5H-benzocycloheptenyl-6-acetate (120 mg, 0.3 mmol), 10% Pd/C (72 mg), cyclohexene (1 mL, 9.8 mmole), and ethanol (25 mL) was heated at reflux for 18 h, then the catalyst was removed by filtration through celite®. The filtrate was concentrated. Flash chromatography of the residue (1:1 EtOAc/hexanes) gave the title compound (55 mg, 55%). $^1$H NMR (400 MHz, CDCl$_3$) δ 8.10 (dd, J=6.6, 1.3 Hz, 1H), 7.42 (m, 1H), 7.10 (d, J=2.6 Hz, 1H), 6.78 (d, J=2.6 Hz, 1H), 6.70 (dd, J=8.2, 2.6 Hz, 1H), 6.58 (dd, J=8.5, 1.6 Hz, 1H), 6.40 (d, J=2.6 Hz, 1H), 4.80 (m,1H), 4.10 (m, 2H), 3.70 (s, 3H), 3.55 (m, 2H), 3.05 (m, 1H), 2.75–2.95 (m, 6H), 2.55 (m,1H), 2.40 (dd, J=15.6, 9.4 Hz, 1H), 2.05–2.15 (m, 2H); MS (ES) m/e 383.3 (M+H)$^+$.

c) (±)-2-(2-Pyridylamino)propoxy-6,7,8,9-tetrahydro-7-oxo-5H-benzocycloheptenyl-6-acetic acid A mixture of methyl (±)-2-(2-pyridylamino)propoxy-6,7,8,9-tetrahydro-7-oxo-5H-benzocycloheptenyl-6-acetate (55 mg, 0.14 mmol) and 1.0 N NaOH (0.4 mL) in MeOH (3 mL) was stirred at RT for 18 h. and neutralized. Desalting through XAD-2 column followed by lyophilization gave the titled compound (35 mg, 70 %). $^1$H NMR (400 MHz, CDCl$_3$) δ 7.92 (dd, J=6.6,1.3 Hz, 1H), 7.45 (m, 1H), 7.10 (d, J=2.6 Hz, 1H), 6.78 (d, J=2.6 Hz, 1H), 6.70 (dd, J=8.2, 2.6 Hz, 1H), 6.58 (dd, J=8.5, 1.6 Hz, 1H), 6.50 (d, J=2.6 Hz, 1H), 4.10 (m, 2 H), 3.50 (m, 2 H), 3.00 (m, 1H), 2.70–2.95 (m, 6 H), 2.55 (m, 1 H), 2.45 (dd, J=15.6, 9.4 Hz, 1H), 2.18–2.15 (m, 2H); MS (ES) m/e 369.2 (M+H)$^+$. Anal. Calcd for C$_{21}$H$_{24}$N$_2$O$_4$·0.5H$_2$O: C, 66.82; H, 6.41; N, 7.42. Found: C, 66.41; H, 6.14; N, 7.42.

Example 3

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound according to formula (1):

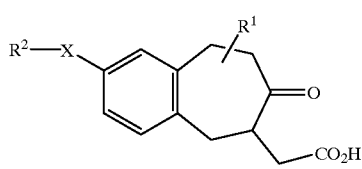

(I)

wherein:

R$^1$ is R$^7$, or A-C$_{0-4}$alkyl, A-C$_{2-4}$alkenyl, A-C$_{2-4}$alkynyl, A-C$_{3-4}$oxoalkenyl, A-C$_{3-4}$oxoalkynyl, A-C$_{1-4}$aminoalkyl, A-C$_{3-4}$aminoalkenyl, A-C$_{3-4}$aminoalkynyl, optionally substituted by any accessible combination of one or more of R$^{10}$ or R$^7$;

X is O, C(O)NR', or NR'C(O);

A is H, C$_{3-6}$cycloalkyl, Het or Ar;

R$^7$ is —COR$^8$, —COCR'$_2$R$^9$, —C(S)R$^8$, —S(O)$_m$OR', —S(O)$_m$NR'R", —PO(OR'), —PO(OR)$_2$, —B(OR)$_2$, —NO$_2$, or tetrazolyl;

each R$^8$ independently is —OR', —NRR", —NR'SO$_2$R', —NR'OR', or —OCR'$_2$CO(O)R';

R$^9$ is —OR', —CN, —S(O)$_r$R', —S(O)$_m$NR'$_2$, —C(O)R', C(O)NR'$_2$, or —CO$_2$R';

R$^{10}$ is H, halo, —OR$^{11}$, —CN, —NR'R$^{11}$, —NO$_2$, —CF$_3$, CF$_3$S(O)$_r$—, —CO$_2$R', —CONR'$_2$, A-C$_{0-6}$alkyl-, A-C$_{1-6}$ oxoalkyl-, A-C$_{2-6}$alkenyl-, A-C$_{2-6}$alkynyl-, A-C$_{0-6}$ alkyloxy-, A-C$_{0-6}$alkylamino- or A-C$_{0-6}$alkyl-S (O)$_r$-;

R$^{11}$ is R', —C(O)R', —C(O)NR'$_2$, —C(O)OR', —S(O)$_m$R', or —S(O)$_m$NR'$_2$;

R$^2$ is

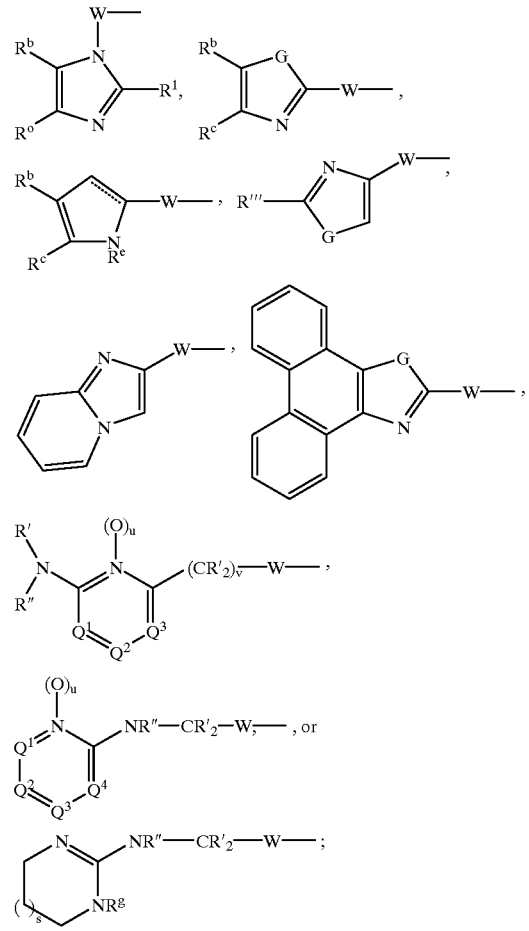

W is —(CHR$^g$)$_a$—U—(CHR$^g$)$_b$—;

U is absent or CO, CR$^g$$_2$, C(=CR$^g$$_2$), S(O)$_k$, O, NR$^g$, CR$^g$OR$^g$, CR$^g$(OR$^k$)CR$^g$$_2$, CR$^g$$_2$CR$^g$(OR$^k$), C(O)CR$^g$$_2$, CR$^g$$_2$C(O), C(O)NR$^i$, NR$^i$C(O), OC(O), C(O)O, C(S) O, OC(S), C(S)NR$^g$, NR$^g$C(S), S(O)$_2$NR$^g$, NR$^g$S(O)$_2$ N=N, NR$^g$NR$^g$, NR$^g$CR$^g$$_2$, NR$^g$CR$^g$$_2$, CR$^g$$_2$O, OCR$^g$$_2$, C≡C or CR$^g$=CR$^g$;

G is NR$^e$, S or O,

R$_g$ is H, C$_{1-6}$alkyl, Het-C$_{0-6}$alkyl, C$_{3-7}$cycloalkyl-C$_{0-6}$ alkyl or Ar-C$_{0-6}$alkyl;

R$^k$ is R$^g$, —C(O)R$^g$, or —C(O)OR$^f$;

$R^i$ is is H, $C_{1-6}$alkyl, Het-$C_{0-6}$alkyl, $C_{3-7}$cycloalkyl-$C_{0-6}$alkyl, Ar-$C_{0-6}$alkyl, or $C_{1-6}$alkyl substituted by one to three groups chosen from halogen, CN, $NR^g{}_2$, $OR^g$, $SR^g$, $CO_2R^g$, and $CON(R^g)_2$;

$R^f$ is H, $C_{1-6}$alkyl or Ar-$C_{1-6}$alkyl;

$R^e$ is H, $C_{1-6}$alkyl, Ar-$C_{1-6}$alkyl, Het-$C_{1-6}$alkyl, $C^{3-7}$cycloalkyl-$C_{1-6}$alkyl, or $(CH_2)_kCO_2R^g$;

$R^b$ and $R^c$ are independently selected from H, $C_{1-6}$alkyl, Ar-$C_{0-6}$alkyl, Het-$C_{0-6}$alkyl, or $C_{3-6}$cycloalkyl-$C_{0-6}$alkyl, halogen, $CF_3$, $OR^f$, $S(O)_kR^f$, $COR^f$, $NO_2$, $N(R^f)_2$, $CO(NR^f)_2$, $CH_2N(R^f)_2$, or $R^b$ and $R^c$ are joined together to form a five or six membered aromatic or non-aromatic carbocyclic or heterocyclic ring, optionally substituted by up to three substituents chosen from halogen, $CF_3$, $C_{1-4}$alkyl, $OR^f$, $S(O)_kR^f$, $COR^f$, $CO_2R^f$, OH, $NO_2$, $N(R^f)_2$, $CO(NR^f)_2$, and $CH_2N(R^f)_2$; or methylenedioxy;

$Q^1$, $Q^2$, $Q^3$ and $Q^4$ are independently N or C—$R^v$, provided that no more than one of $Q^1$, $Q^2$, $Q^3$ and $Q^4$ is N;

R' is H, $C_{1-6}$alkyl, Ar-$C_{0-6}$alkyl or $C_{3-6}$cycloalkyl-$C_{0-6}$alkyl;

R" is R', —C(O)R' or —C(O)OR';

R'" is H, $C_{1-6}$alkyl, Ar-$C_{0-6}$alkyl, Het-$C_{0-6}$alkyl, or $C_{3-6}$cycloalkyl-$C_{0-6}$alkyl, halogen, $CF_3$, $OR^f$, $S(O)_kR^f$, $COR^f$, $NO_2$, $N(R^f)_2$, $CO(NR^f)_2$, $CH_2N(R^f)_2$;

$R^v$ is H, halo, —$OR^g$, —$SR^g$, —CN, —$NR^gR^k$, —$NO_2$, —$CF_3$, $CF_3S(O)_r$—, —$CO_2R^g$, —$COR^g$ or —$CONR^g{}_2$, or $C_{1-6}$alkyl optionally substituted by halo, —$OR^g$, —$SR^g$, —CN, —$NR^gR"$, —$NO_2$, —$CF_3$, R'S$(O)_r$—, —$CO_2R^g$, —$COR^g$ or —$CONR^9{}_2$;

a is 0, 1 or 2;

b is 0, 1 or 2;

k is 0, 1 or 2;

m is 1 or 2;

r is 0, 1 or 2;

s is 0, 1 or 2;

u is 0 or 1;and v is 0 or 1;

or a pharmaceutically acceptable salt thereof.

2. A compound according to claim 1 in which X is O.

3. A compound according to claim 2 in which $R^2$ is

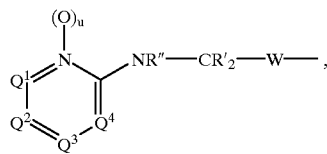

wherein $Q^1$, $Q^2$, and $Q^3$ are each $CR^v$, $Q^4$ is $CR^v$ or N and u is 0.

4. A compound according to claim 3 in which each R' is H, R" is H, $C_{1-6}$alkyl, —$C(O)C_{1-6}$alkyl, $C(O)OC_{1-6}$alkyl, —$C(O)C_{0-6}$alkyl-Ar, or $C(O)OC_{0-6}$alkyl-Ar, W is —$CH_2$—$CH_2$—, and $R^y$ is H, halo, —$OR^g$, —$SR^g$, —CN, —$NR^gR^k$, —$NO_2$, —$CF_3$, $CF_3S(O)_r$—, —$CO_2R^g$, —$COR^g$—$CONR^g{}_2$, or $C_{1-6}$alkyl.

5. A compound according to claim 1 in which $R^2$ is

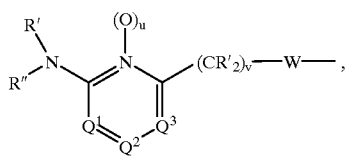

wherein $Q^1$, $Q^2$, and $Q^3$ are each CH and u is 0.

6. A compound according to claim 5 in which each R' is H, R" is H or $C_{1-4}$alkyl and W is —$CH_2$—$CH_2$—.

7. A compound according to claim 1 which is (±)-2-(2-pyridylamino)propoxy-6,7,8,9-tetrahydro-7-oxo-5H-benzocycloheptenyl-6-acetic acid or a pharmaceutically acceptable salt thereof.

8. A pharmaceutical composition which comprises a compound according to claim 1 and a pharmaceutically acceptable carrier.

9. A method of treating a disease state in which antagonism of the vitronectin receptor is indicated which comprises administering a compound according to claim 1.

10. A method of inhibiting angiogenesis which comprises administering a compound according to claim 1.

11. A method of treating atherosclerosis, restenosis, inflammation, cancer or osteoporosis which comprises administering a compound according to claim 1.

12. A compound according to formula (II):

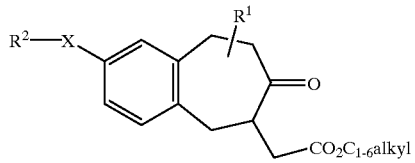

(II)

wherein:

$R^1$ is $R^7$, or A-$C_{0-4}$alkyl, A-$C_{2-4}$alkenyl, A-$C_{2-4}$alkynyl, A-$C_{3-4}$oxoalkenyl, A-$C_{3-4}$oxoalkynyl, A-$C_{1-4}$aminoalkyl, A-$C_{3-4}$aminoalkenyl, A-$C_{3-4}$aminoalkynyl, optionally substituted by any accessible combination of one or more of $R^{10}$ or $R^7$;

X is O, C(O)NR', or NR'C(O);

A is H, $C_{3-6}$cycloalkyl, Het or Ar;

$R^7$ is —$COR^8$, —$COCR'_2R^9$, —$C(S)R^8$, —$S(O)_mOR'$, —$S(O)_mNR'R"$, —$PO(OR')$, —$PO(OR')_2$, —$B(OR')_2$, —$NO_2$, or tetrazolyl;

each $R^8$ independently is —OR', —NR'R", —$NR'SO_2R'$, —NR'OR', or —$OCR'_2CO(O)R'$;

$R^9$ is —OR', —CN, —$S(O)_rR'$, —$S(O)_mNR'_2$, —C(O)R', C(O)NR'_2, or —$CO_2R'$;

$R^{10}$ is H, halo, —$OR^{11}$, —CN, —$NR'R^{11}$, —$NO_2$, —$CF_3$, $CF_3S(O)_r$—, —$CO_2R'$, —$CONR'_2$, A-$C_{0-6}$alkyl-, A-$C_{1-6}$oxoalkyl-, A-$C_{2-6}$alkenyl-, A-$C_{2-6}$alkynyl-, A-$C_{0-6}$alkyloxy-, A-$C_{0-6}$alkylamino- or A-$C_{0-6}$alkyl-S$(O)_r$-;

$R^{11}$ is R', —C(O)R', —$C(O)NR'_2$, —C(O)OR', —$S(O)_mR'$, or —$S(O)_mNR'_2$;

$R^2$ is

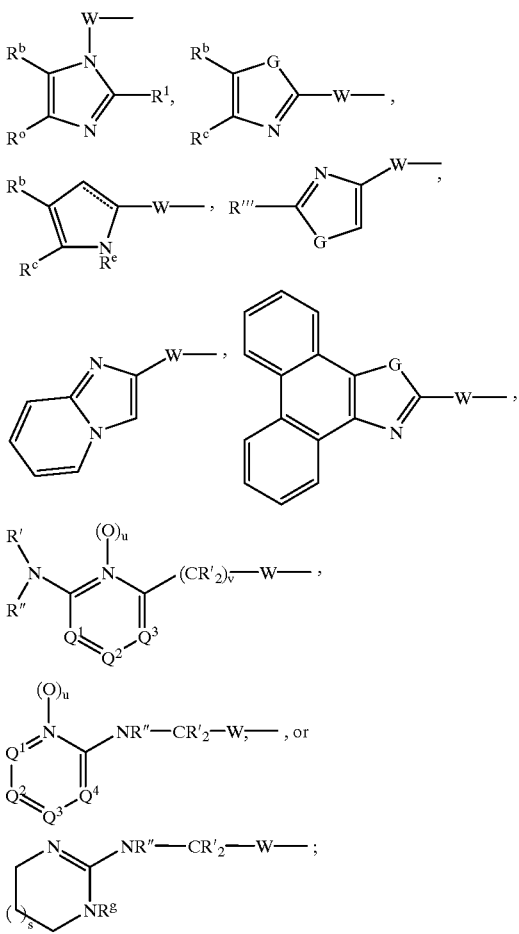

W is —$(CHR^g)_a$—U—$(CHR^g)_b$—;
U is absent or CO, $CR^g_2$, C(=$CR^g_2$), S(O)$_k$, O, $NR^g$, $CR^gOR^g$, $CR^g(OR^k)CR^g_2$, $CR^g_2CR^g(OR^k)$, C(O)$CR^g_2$, $CR^g_2$C(O), CON $R^i$ N $R^i$ CO OC(O), C(O)O, C(S)O, OC(S), C(S)$NR_9$, $NR^g$C(S), S(O)$_2NR^g$, $NR^gS(O)_2$ N=N, $NR^gNR^g$, $NR^gCR^g_2$, $NR^{gCR^g}_2$, $CR^g_2$O, $OCR^g_2$, C≡C or $CR^g$=$CR^g$;
G is $NR^e$, S or O;
$R^g$ is H, $C_{1-6}$alkyl, Het-$C_{0-6}$alkyl, $C_{3-7}$cycloalkyl-$C_{0-6}$alkyl or Ar-$C_{0-6}$alkyl;
$R^k$ is $R^8$, —C(O)$R^g$, or —C(O)O$R^f$;
$R^i$ is is H, $C_{1-6}$alkyl, Het-$C_{0-6}$alkyl, $C_{3-7}$cycloalkyl-$C_{0-6}$alkyl, Ar-$C_{0-6}$alkyl, or $C_{1-6}$alkyl substituted by one to three groups chosen from halogen, CN, $NR^g_2$, $OR^g$, $SR^g$, $CO_2R^g$, and CON($R^g)_2$;
$R^f$ is H, $C_{1-6}$alkyl or Ar-$C_{1-6}$alkyl;
$R^e$ is H, $C_{1-6}$aikyl, Ar-$C_{1-6}$alkyl, Het-$C_{1-6}$alkyl, $C_{3-7}$cycloalkyl-$C_{1-6}$alkyl, or $(CH_2)_kCO_2R^g$;
$R^b$ and $R^c$ are independently selected from H, $C_{1-6}$alkyl, Ar-$C_{0-6}$alkyl, Het-$C_{0-6}$alkyl, or $C_{3-6}$cycloalkyl-$C_{0-6}$alkyl, halogen, $CF_3$, $OR^f$, S(O)$_kR^f$, $COR^f$, $NO_2$, N($R^f)_2$, CO(N$R^f)_2$, $CH_2N(R^f)_2$, or $R^b$ and $R^c$ are joined together to form a five or six membered aromatic or non-aromatic carbocyclic or heterocyclic ring, optionally substituted by up to three substituents chosen from halogen, $CF_3$, $C_{1-4}$alkyl, $OR^f$, S(O)$_kR^f$, $COR^f$, $CO_2R^f$, OH, $NO_2$, N($R^f)_2$, CO(N$R^f)_2$, and $CH_2N(R^f)_2$; or methylenedioxy;

$Q^1$, $Q^2$, $Q^3$ and $Q^4$ are independently N or C—$R^y$, provided that no more than one of $Q^1$, $Q^2$, $Q^3$ and $Q^4$ is N;
R' is H, $C_{1-6}$alkyl, Ar-$C_{0-6}$alkyl or $C_{3-6}$cycloalkyl-$C_{0-6}$alkyl;
R'' is R', —C(O)R' or —C(O)OR';
R''' is H, $C_{1-6}$alkyl, Ar-$C_{0-6}$alkyl, Het-$C_{0-6}$alkyl, or $C_{3-6}$cycloalkyl-$C_{0-6}$alkyl, halogen, $CF_3$, $OR^f$, S(O)$_kR^f$, $COR^f$, $NO_2$, N($R^f)_2$, CO(N$R^f)_2$, $CH_2N(R^f)_2$;
$R^y$ is H, halo, —$OR^g$, —$SR^g$, —CN, —$NR^gR^k$, —$NO_2$, —$CF_3$, $CF_3$S(O)$_r$—, —$CO_2R^g$, —$COR^G$ or —CON$R^g_2$, or $C_{1-6}$alkyl optionally substituted by halo, —$OR^g$, —$SR^g$, —CN, —$NR^g$R'', —$NO_2$, —$CF_3$, R'S(O)$_r$—, —$CO_2R^g$, —$COR^g$ or —CON$R^g_2$;
a is 0, 1 or 2;
b is 0, 1 or 2;
k is 0, 1 or 2;
m is 1 or 2;
r is 0, 1 or 2;
s is 0, 1 or 2;
u is 0 or 1; and
v is 0 or 1;
or a pharmaceutically acceptable salt thereof.

13. A compound according to claim 11 which is methyl (±)-2-(2-pyridylamino)propoxy-6,7,8,9-tetrahydro-7-oxo-5H-benzocycloheptenyl-6-acetate or a pharmaceutically acceptable salt thereof.

14. A compound according to formula (III):

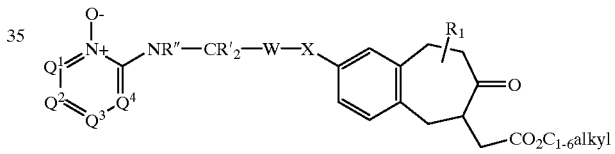

(III)

$R^1$ is $R^7$, or A-$C_{0-4}$alkyl, A-$C_{2-4}$alkenyl, A-$C_{2-4}$alkynyl, A-$C_{3-4}$oxoalkenyl, A-$C_{3-4}$oxoalkynyl, A-$C_{1-4}$ aminoalkyl, A-$C_{3-4}$aminoalkenyl, A-$C_{3-4}$ aminoalkynyl, optionally substituted by any accessible combination of one or more of $R^{10}$ or $R^7$;
X is O, C(O)NR', or NR'C(O);
A is H, $C_{3-6}$cycloalkyl, Het or Ar;
$R^7$ is —$COR^8$, —COCR'$_2R^9$, —C(S)$R^8$, —S(O)$_m$OR', —S(O)$_m$NR'R'', —PO(OR'), —PO(OR')$_2$, —B(OR')$_2$, —$NO_2$, or tetrazolyl;
each $R^8$ independently is —OR', —NR'R'', —NR'SO$_2$R', —NR'OR', or —OCR'$_2$CO(O)R';
$R^9$ is —OR', —CN, —S(O)$_r$R', —S(O)$_m$NR'$_2$, —C(O)R', C(O)NR'$_2$, or —CO$_2$R';
$R^{10}$ is H, halo, —$OR^{11}$, —CN, —NR'R$^{11}$, —$NO_2$, —$CF_3$, $CF_3$S(O)$_r$—, —$CO_2$R', —CONR'$_2$, A-$C_{0-6}$alkyl-, A-$C_{1-6}$ oxoalkyl-, A-$C_{2-6}$alkenyl-, A-$C_{2-6}$alkynyl-, A-$C_{0-6}$ alkyloxy-, A-$C_{0-6}$alkylamino or A-$C_{0-6}$alkyl-S(O)$_r$-;
$R^{11}$ is R', —C(O)R', —C(O)NR'$_2$, —C(O)OR', —S(O)$_m$R' or —S(O)$_m$NR'$_2$;
W is —$(CHR^g)_a$—U—$(CHR^g)_b$—;
U is absent or CO, $CR^g_2$, C(=$CR^g_2$), S(O)$_k$, O, $NR^g$, $CR^gOR^g$, $CR^g(OR^k)CR^g_2$, $CR^g_2CR^g(OR^k)$, C(O)$CR^g_2$, $CR^g_2$C(O), CON $R^i$ N $R^i$ CO OC(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g_2$, NR$^g$CR$^g_2$, CR$^g_2$O, OCR$^g_2$, C≡C or CR$^g$=CR$^g$;

R$^g$ is H, C$_{1-6}$alkyl, Het-C$_{0-6}$alkyl, C$_{3-7}$cycloalkyl-C$_{0-6}$alkyl or Ar-C$_{0-6}$alkyl;

R$^k$ is R$^g$, —C(O)R$^g$, or —C(O)OR$^f$;

R$^i$ is is H, C$_{1-6}$alkyl, Het-C$_{0-6}$alkyl, C$_{3-7}$cycloalkyl-C$_{0-6}$alkyl, Ar-C$_{0-6}$alkyl, or C$_{1-6}$alkyl substituted by one to three groups chosen from halogen, CN, NR$^g_2$, OR$^g$, SR$^g$, CO$_2$R$^g$, and CON(R$^g$)$_2$;

R$^f$ is H, C$_{1-6}$alkyl or Ar-C$_{1-6}$alkyl;

Q$^1$, Q$^2$, Q$^3$ and Q$^4$ are independently N or C-RY, provided that no more than one of Q$^1$, Q$^2$, Q$^3$ and Q$^4$ is N;

R' is H, C$_{1-6}$alkyl, Ar-C$_{0-6}$alkyl or C$_{3-6}$cycloalkyl-C$_{0-6}$alkyl;

R" is R', —C(O)R' or —C(O)OR';

R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g_2$, or C$_{1-6}$alkyl optionally substituted by halo, —OR$^g$, —SR$^g$, —CN, —NR$^g$R", —NO$_2$, —CF$_3$, R'S(O)$_r$—, -CO$_2$R$^g$, —COR$^g$ or —CONR$^g_2$;

a is 0, 1 or 2;

b is 0, 1 or 2;

m is 1 or 2; and r is 0, 1 or 2;

or a pharmaceutically acceptable salt thereof.

* * * * *